(12) United States Patent
Mukherjee et al.

(10) Patent No.: US 9,546,193 B2
(45) Date of Patent: Jan. 17, 2017

(54) COMPOSITIONS AND METHODS FOR 18F-FLUORODEOXYGLYCOSYLAMINES

(71) Applicant: The Regents of the University of California, Oakland, CA (US)

(72) Inventors: Jogeshwar Mukherjee, Irvine, CA (US); Aparna Baranwal, Cerritos, CA (US); Nehal Mahendra Shah, Irvine, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 14/522,905

(22) Filed: Oct. 24, 2014

(65) Prior Publication Data

US 2015/0291647 A1    Oct. 15, 2015

Related U.S. Application Data

(60) Provisional application No. 61/895,207, filed on Oct. 24, 2013.

(51) Int. Cl.
*C07H 15/26* (2006.01)
*C07B 59/00* (2006.01)
(Continued)

(52) U.S. Cl.
CPC ............ *C07H 15/26* (2013.01); *A61K 51/04* (2013.01); *A61K 51/0446* (2013.01);
(Continued)

(58) Field of Classification Search
CPC ... C07H 15/26; C07B 59/005; A61K 51/0448; A61K 51/0468; A61K 51/0491; A61K 51/0453; A61K 51/0446; A61K 51/04; C07C 227/18; C07C 245/08; C07C 215/16; C07C 213/02; C07D 207/09; C07D 471/08; C07D 277/66
See application file for complete search history.

(56) References Cited

U.S. PATENT DOCUMENTS 8,038,983 B2    10/2011  McBride et al.
2009/0068110 A1*  3/2009  Shang ............ A61K 31/337
                                              424/9.2
(Continued)

FOREIGN PATENT DOCUMENTS

EP    1660519       5/2014
WO    2005086612    9/2005
WO    2008132541    11/2008

OTHER PUBLICATIONS

List Baranwal, Aparna, Liang, Christopher, Pan, Min-liang, Mirbolooki, M. Reza, Constantinescu, Cristian, Mukherjee, Jogeshwar; 18F-Fluorodeoxyglycosylamines: Maillard reaction of 18F-FDG with biological amines J Nucl Med Meeting Abstracts 2013 54: 1071.

*Primary Examiner* — Johann R Richter
*Assistant Examiner* — Katherine Peebles
(74) *Attorney, Agent, or Firm* — Fisk & Tsang LLP

(57) ABSTRACT

Various compositions and methods for Quasi-Amadori products and derivatives thereof are contemplated in which a halogenated carbohydrate is reacted with a primary amino group of an affinity ligand. In especially preferred aspects, the Quasi-Amadori product is formed from 2-fluorodeoxyglucose and an affinity moiety that preferentially or selectively binds to a neural cell or neural structure. Where contemplated compounds include $^{18}F$, PET imaging using compounds presented herein is especially preferred.

4 Claims, 7 Drawing Sheets

(51) Int. Cl.
*A61K 51/04* (2006.01)
*C07C 227/18* (2006.01)
*C07D 207/09* (2006.01)
*C07C 245/08* (2006.01)
*C07D 471/08* (2006.01)
*C07C 215/16* (2006.01)
*C07D 277/66* (2006.01)
*C07C 213/02* (2006.01)

(52) U.S. Cl.
CPC ...... *A61K 51/0448* (2013.01); *A61K 51/0453* (2013.01); *A61K 51/0468* (2013.01); *A61K 51/0491* (2013.01); *C07B 59/005* (2013.01); *C07C 215/16* (2013.01); *C07C 227/18* (2013.01); *C07C 245/08* (2013.01); *C07D 207/09* (2013.01); *C07D 277/66* (2013.01); *C07D 471/08* (2013.01); *C07C 213/02* (2013.01)

(56) References Cited

U.S. PATENT DOCUMENTS

| | | | |
|---|---|---|---|
| 2009/0130019 A1* | 5/2009 | Tobinick | A61K 51/1018 424/1.49 |
| 2013/0149243 A1 | 6/2013 | Berndt et al. | |
| 2014/0024803 A1 | 1/2014 | Bhushan et al. | |

* cited by examiner

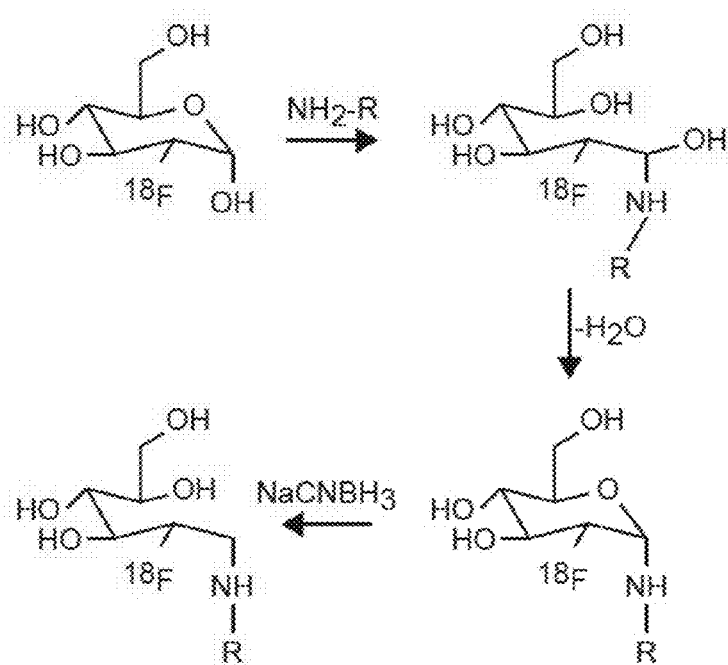
FIG. 7
FIG. 8C
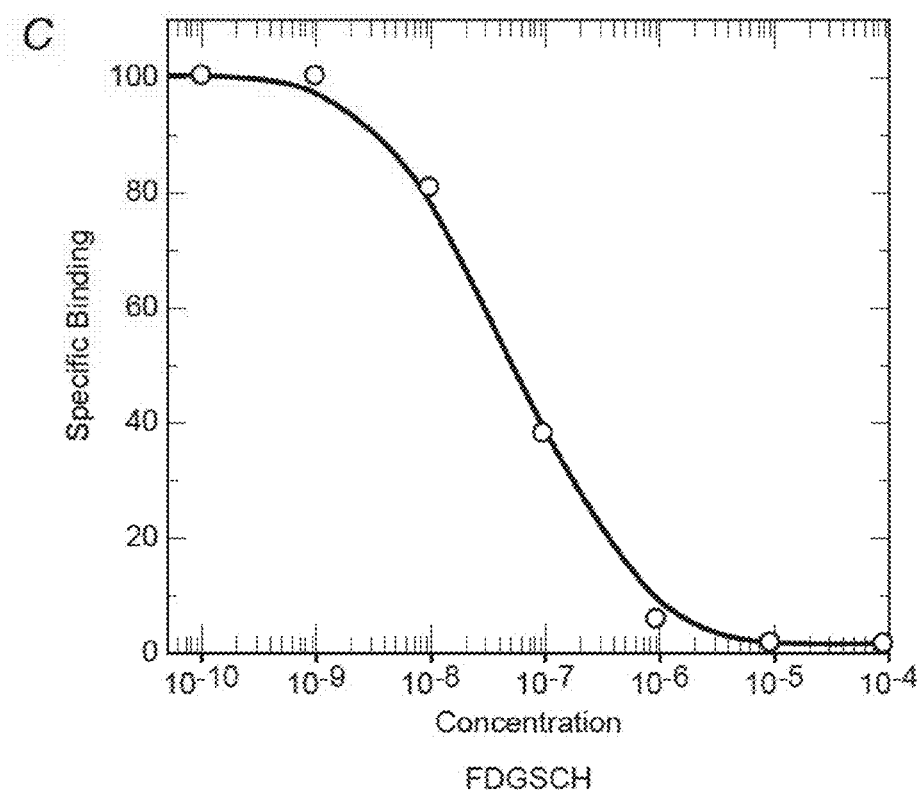
FDGSCH

COMPOSITIONS AND METHODS FOR 18F-FLUORODEOXYGLYCOSYLAMINES

This application claims priority to our U.S. provisional application having Ser. No. 61/895,207, which was filed Oct. 24, 2013.

This invention was made with government support under AG029479 and DK092917 awarded by the NIH. The government has certain rights in the invention.

FIELD OF THE INVENTION

The field of the invention is composition and methods for glycosylamines, and especially glycosylamines of FDG (fluorodeoxyglucose).

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

2-$^{18}$F-Fluorodeoxyglucose ($^{18}$F-FDG) is a well-known compound and has found various uses in medical imaging, and especially in imaging of tumors as $^{18}$F-FDG is rapidly absorbed into malignant cells. $^{18}$F-FDG is also taken up into various neural tissues and has become one of the preferred imaging agents in PET neuroimaging. Synthesis of $^{18}$F-FDG is well-understood and various synthetic pathways are known to obtain labeled product with relatively high isotopic yield.

In addition to FDG or isotopically labeled FDG, certain reaction products of FDG with peptides coupled to the FDG moiety via a hydrazine or hydrazone bond were described in WO 2005/086612. While such compounds are conceptually suitable for targeted radio labeling, the stability in vivo of at least some of the compounds is uncertain and synthesis is often non-trivial. In a similar manner, WO 2008/132541 teaches conjugates of antineoplastic agents with FDG where the antineoplastic moiety is attached to the FDG via specific linker structures. While such compounds may be suitable as chemotherapeutic agents, utility as labeling agents only tends to be reduced due to the toxicity of such compounds. Further known FDG conjugates are described in US 2014/0024803 where FDG is coupled to certain moieties via an amide bond to so produce multivalent radiotracers for targeted cancer imaging. In these compounds, the targeting ligand is conjugated with an NHS ester of a multivalent scaffold. While such compounds may improve at least labeling of at least certain cancers, synthesis is not simple and in vivo stability may be hard to achieve for a reasonable period of time. The above references and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

The Maillard reaction of sugars and amines results in the formation of glycosylamines and Amadori products, which are frequently of biological significance. Formation of Amadori product typically occurs by reaction of an amine with an aldehyde at the 1-position of glucose to form a Schiff base as exemplarily shown in Prior Art FIG. 1A. The Schiff base is then subject to water loss and rearrangement of the hydroxyl at the 2-position to so form the corresponding ketone. Prior Art FIG. 1B exemplarily depicts the Amadori products desoxyfructoseserotonin and fructoselysine. Notably, it has been shown that glucose reacts with serotonin in a Maillard reaction and produce the Amadori product desoxyfructoserotonin that has been used to elevate brain serotonin levels in mice studies. Other Maillard reaction products have been observed and assessed in aging, diabetes, and Alzheimer's disease pathologies.

Therefore, while numerous reaction products and methods associated with $^{18}$F-FDG or F-FDG are already known, there is still a need to provide improved $^{18}$F-FDG or F-FDG derivatives, especially where such derivatives have increased in vivo stability and are suitable for labeling of various tissues, and particularly neural tissue.

SUMMARY OF THE INVENTION

The inventive subject matter is directed to various compositions, aspects, and methods of derivatizing 2-F-Fluorodeoxyglucose and 2-$^{18}$F-Fluorodeoxyglucose, and particularly preferred compounds and methods will be useful in radio imaging, and especially in vivo imaging. Among other contemplated compounds and methods, F-FDG and $^{18}$F-FDG are reacted with a moiety that exhibits preferential or even selective binding to a target cell and/or structure to form a Quasi-Amadori product, which may be further subjected to reduction. Viewed from another perspective it should be appreciated that various radio imaging agents can be formed by reductive amination via Quasi-Amadori products of $^{18}$F-FDG.

In one aspect of the inventive subject matter, contemplated compounds have a structure according to Formula I or Formula II

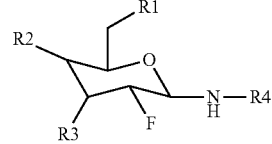

Formula I

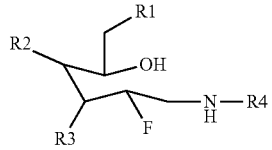

Formula II wherein $R_1$, $R_2$, and $R_3$ are independently H or OH, wherein F is $^{18}$F or $^{19}$F, and wherein $R_4$ is an affinity ligand. Most typically, at least two of $R_1$, $R_2$, and $R_3$ are OH, and in further contemplated aspects, $R_1$, $R_2$, and $R_3$ are OH, while in further preferred aspects, a carbon atom of $R_4$ is covalently bound to NH. Therefore, in other aspects it is also contemplated that the carbohydrate moiety in Formula I or II is 2-fluorodeoxyglucose (e.g., 2-$^{18}$F-fluorodeoxyglucose).

While not limiting to the inventive subject matter, it is generally preferred that the affinity ligand is a ligand for a component or receptor in a neural tissue. For example, suitable affinity ligands include ligands for Alzheimer's disease plaque, or ligands for a dopamine receptor or a norepinephrine receptor.

Thus, especially contemplated compounds include those of Formula III-IX, where F may be $^{18}$F or $^{19}$F

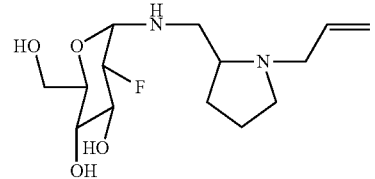

FDGNAP

Formula III

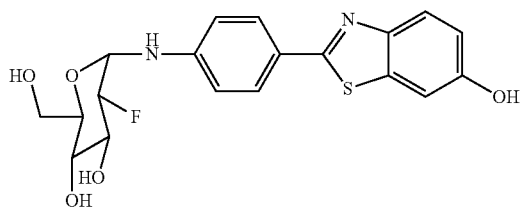

FDGBTA

Formula IV

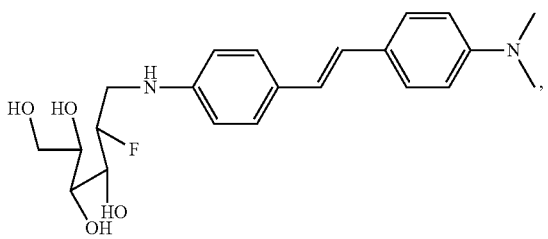

Formula V

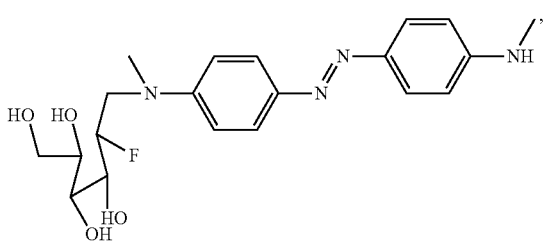

Formula VI

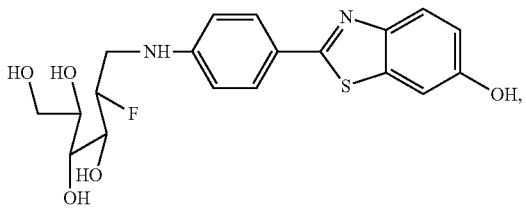

Formula VII

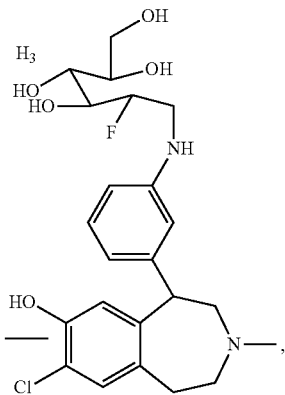

Formula VIII

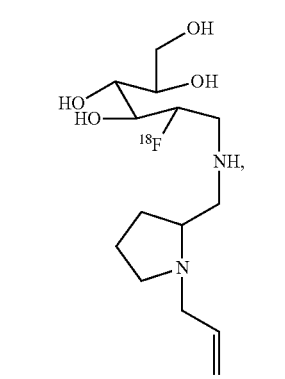

Formula IX

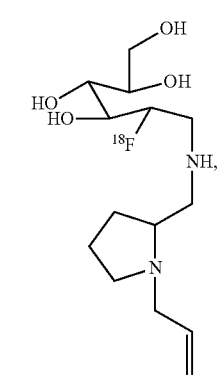

Formula X

In another aspect of the inventive subject matter, contemplated compounds may be formulated into a pharmaceutical composition in combination with a pharmaceutically acceptable carrier. Most typically, F is $^{18}$F and the compound is present in an amount effective to produce an in vivo detectable PET signal. For example, F is $^{18}$F and the compound may be present in an amount effective to allow imaging human Aβ-amyloid plaque.

In yet another aspect of the inventive subject matter, the inventors also contemplate a method of synthesizing a compound in which a halogenated carbohydrate is reacted with an affinity ligand having a (preferably primary) amine group, wherein the halogenated carbohydrate is halogenated at a C-2 atom, and wherein the affinity ligand is a ligand for a component or receptor in a neural tissue. Most typically, the step of reacting is performed under conditions that allow formation of a Quasi-Amadori product. Where desired, the Quasi-Amadori product may then be reduced under conditions that allow formation of a reductive amination product.

Most preferably, the halogenated carbohydrate is a fluorinated deoxyglucose (e.g., 2-$^{18}$F-fluorodeoxyglucose). Among other reaction conditions, especially preferred conditions include a step of reacting the halogenated carbohydrate with the affinity ligand in an alcoholic solvent at a temperature of 20-130° C., and/or especially preferred reduction conditions include a step of reacting the Quasi-Amadori product with NaBH₃CN.

Various objects, features, aspects and advantages of the inventive subject matter will become more apparent from the following detailed description of preferred embodiments, along with the accompanying drawing in which like numerals represent like components.

BRIEF DESCRIPTION OF THE DRAWING

Prior Art FIG. 1 exemplarily shows a Maillard reaction sequence leading to an Amadori reaction product in Panel A, and depicts exemplary Amadori reaction products in Panel B.

FIG. 7 exemplarily shows a reaction sequence leading to a reductive amination product of $^{18}$F-FDG via reduction of the corresponding Quasi-Amadori product.

DETAILED DESCRIPTION

The inventors have discovered that various FDG compounds having a $^{18}$F or $^{19}$F atom can be prepared in a procedurally very simple and effective manner that produces desired derivatives in high (radiographic) yield. Moreover, especially where the derivatives are products of reductive amination of $^{18}$F-FDG, such products will have increased stability for in vivo imaging.

In most preferred aspects, a Maillard-type reaction of various sugars and amines can be employed for the formation of glycosylamines and Quasi-Amadori products. Thus, and viewed from another perspective, $^{18}$F-FDG (and other halogenated carbohydrates with a halogen at the C-2 atom, which may or may not be a halogen isotope) can be reacted with numerous preferably biological amines to so yield $^{18}$F-fluorodeoxyglycosylamines ($^{18}$F-FDGly) and related products.

Figure 1:
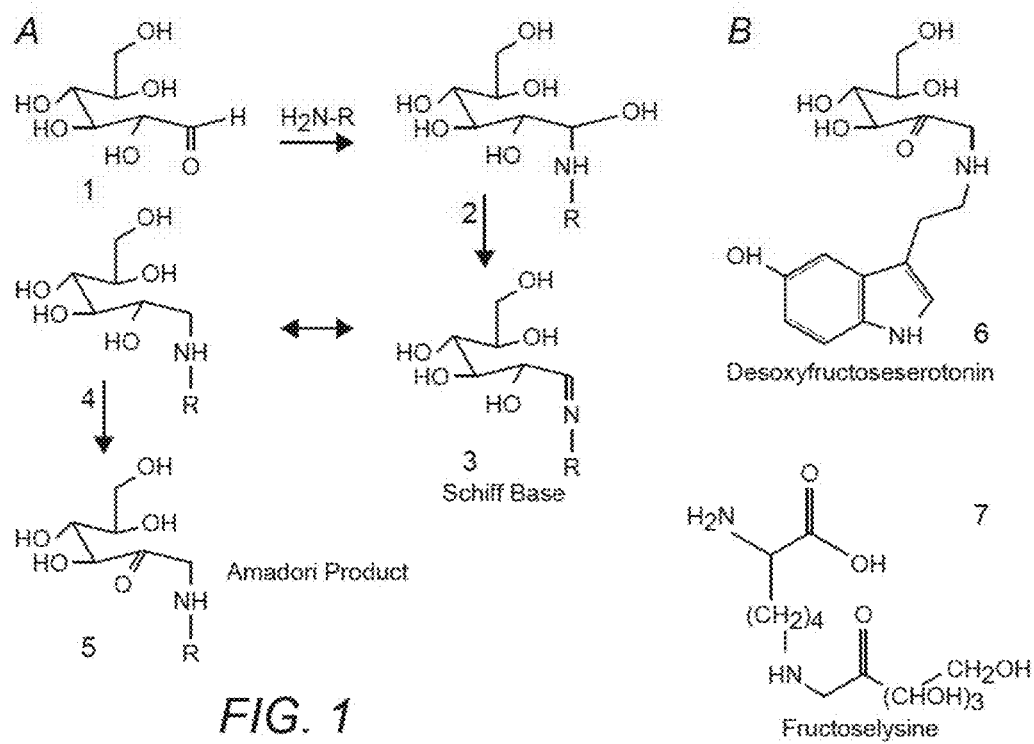
Figure 2:
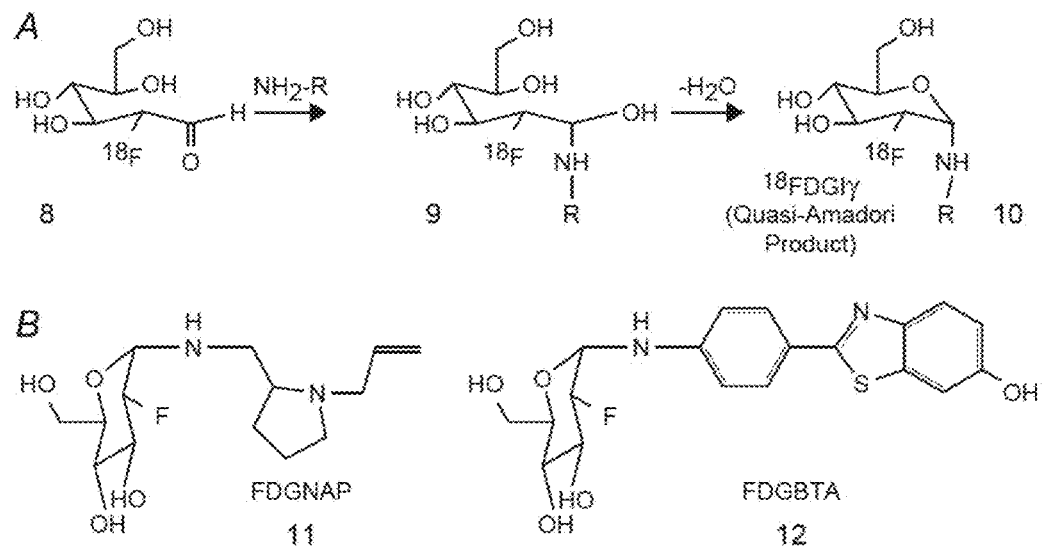
FIG. 2 exemplarily shows a reaction sequence leading to a Quasi-Amadori product in Panel A, and depicts exemplary Quasi-Amadori reaction products in Panel B.

For example, 2-$^{18}$F-Fluorodeoxyglucose, a 2-deoxy analog of glucose is used clinically in various studies for evaluating alterations in glucose metabolic rates using PET (positron emission tomography). Upon administration, $^{18}$F-FDG is phosphorylated by hexokinase and is trapped in a cell in the form of $^{18}$F-FDG-6-phosphate because of the absence of the hydroxyl group at the C-2 atom of glucose. Notably, since $^{18}$F-FDG has an aldehyde group, but lacks the hydroxyl group at the C-2 atom, $^{18}$F-FDG is potentially capable of undergoing a Maillard reaction with amines to so form a Schiff base ($^{18}$F-FDGly, a quasi-Amadori product) without progressing to the classical Amadori product as is exemplarily shown in FIG. 2. Here, as illustrated in Panel (A), primary amine R—NH₂ reacts with $^{18}$F-FDG (8) leading to the $^{18}$F-FDGly Quasi-Amadori product (10) via expulsion of water upon ring closure of hydroxylamine (9). Panel (B) depicts two exemplary synthesized FDGly products reported in more detail below, FDGNAP (11) and FDGBTA (12).

Based on the above experimental results with FDGNAP and FDGBTA, the inventors then proceeded to synthesize various additional Quasi-Amadori products to include compounds that could interact with Aβ-amyloid plaque and various receptors of neural tissue and cells (e.g., norepinephrine receptors, serotonin receptors, etc.). Moreover, the synthesis of $^{18}$F radiolabeled compounds was found to perform equally well with desirable radiographic yields and desirable binding to corresponding structures in neural tissue as reported in more detail below.

For example, respective amines (N-allyl-2-aminomethylpyrrolidine (NAP) and 2-(4'-aminophenyl)-6-hydroxybenzothiazole (PIB precursor)), were reacted with FDG to provide the corresponding glycosylamines, FDGNAP and FDGBTA. Radiosynthesis using $^{18}$F-FDG (2-5 mCi) was carried out to provide $^{18}$F-FDGNAP and $^{18}$F-FDGBTA, respectively. Binding of FDGBTA and $^{18}$F-FDGBTA was evaluated in human brain sections of Alzheimer's disease (AD) patients and control subjects using autoradiography. Notably, both FDGNAP and FDGBTA were isolated as stable products, and the inventors found that $^{18}$F-FDG couples with various primary and secondary amines under mild conditions to form $^{18}$F-FDGly in a manner similar to click chemistry. Kinetics of $^{18}$F-FDGNAP reaction indicated significant product at 4 hrs (63% radiochemical yield), and $^{18}$F-FDGBTA was prepared in 57% yield. Preliminary studies of FDGBTA showed displacement of $^3$H-PIB (reduced by 80%) and $^{18}$F-FDGBTA indicated selective binding to Aβ-amyloid plaques present in postmortem AD (Alzheimer Disease) human brain, with a grey matter ratio of 3 between AD and control subjects.

Contemplated Compounds

Based on the above experimental findings, the inventors therefore contemplate various compounds in which a 2-F-aldose carbohydrate or carbohydrate analog is reacted in a Maillard-type reaction with a primary (or secondary or tertiary) amine of an affinity ligand to produce the corresponding Quasi-Amadori product, which may be further reduced under mild condition to form the corresponding reduced product.

Therefore, in especially preferred aspects, the inventors contemplate compounds having a structure of Formula I and Formula II

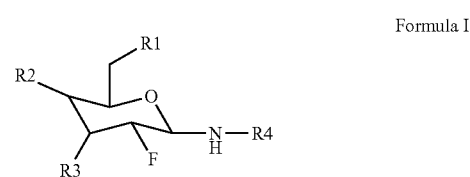

Formula I

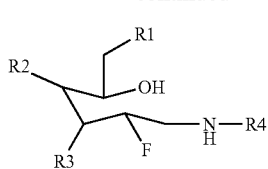

Formula II in which $R_1$, $R_2$, and $R_3$ are independently H or OH, wherein F is $^{18}F$ or $^{19}F$, and wherein $R_4$ is an affinity ligand (and especially an affinity ligand for a neural cell or tissue, or receptor or structure in a neural cell or tissue).

Of course, it should be appreciated that instead of a 2-F-FDG moiety numerous other carbohydrate moieties are deemed suitable so long as such alternative carbohydrates and carbohydrate analogs are capable of undergoing the Amadori-type reaction. Thus, especially preferred alternative carbohydrates include various C3-C7 aldoses, and especially those having a halogen or other label on the C-2 atom. Likewise, it should be noted that the carbohydrate need not be limited to a monosaccharide, but that oligo and polysaccharides are also deemed suitable so long as such saccharides include at least one pendant or terminal aldose. Viewed from a different perspective, it should therefore also be appreciated that numerous isomeric forms are appropriate for use herein and that the particular orientation of a hydroxyl group (alpha or beta) is not limiting.

With respect to the affinity ligand it is generally preferred that the ligand will interact or bind to a neural cell or tissue with preferential (e.g., $K_D<10^{-4}$ M or $K_D<10^{-5}$ M) or even specific binding (e.g., $K_D<10^{-6}$ M or $K_D<10^{-7}$ M). Thus, suitable ligands include small molecule ligands known to bind to receptors, AD plaque and/or specific AD plaque components, etc. In further contemplated aspects, suitable ligands will ligands other than chemotherapeutic agents (having growth inhibiting $IC_{50}$ at concentrations of less than 1 nM, or less than 0.01 μM, or less than 0.10 μM, or less than 1.00 μM). For example, suitable ligands include those described in U.S. Pat. No. 8,378,109 and in US2013/031586, as well as those further described herein.

It should also be recognized that the compounds contemplated herein may be active or be prepared as a metabolites, prodrugs, or otherwise modified compound, wherein the metabolite, prodrug, or modified compound exhibits higher permeability across the blood brain barrier or less toxicity as compared to the unmodified compound and wherein the prodrug or modified compound is converted within the target cell/organ/structure back into the unmodified form. For example, conversion of contemplated compounds into prodrugs may be useful where the active drug is too toxic for safe systemic administration, or where the contemplated compound is less rapidly transported across the blood brain barrier, or where the body breaks down the compound before reaching its target. Contemplated compounds may also be transformed by the hepatic phase I and/or phase II enzyme system, or by gastric acidity, intestinal microbial environment, or other biochemical process. Thus, suitable compounds may be oxidized, hydroxylated, ligated to a carbohydrate, etc. Similarly, contemplated compounds may be formulated such as to facilitate transport across the blood brain barrier, and all known formulations are deemed suitable for use herein.

Contemplated Compositions

Based on the observed and/or expected improved solubility and specificity of compounds contemplated herein, it should be recognized that these compounds may be employed for various pharmaceutical, diagnostic, and research uses. Among other uses, it is contemplated that the compounds will allow early diagnosis of formation of senile plaques and/or neurofibrillary tangles, and will allow to more precisely locate and even quantify such plaques and tangles. In still further contemplated aspects, it is also thought that the compounds presented herein may be employed to reduce or even prevent formation of senile plaques and/or neurofibrillary tangles. Additionally, the compounds may be employed to locate and/or quantify various receptors (e.g., serotonin or norepinephrine receptor or transporters) and specific binding/uptake may be used for diagnostic and therapeutic uses for disorders or conditions associated with the receptor and/or transporter. Thus, it is contemplated that the compounds and compositions according to the inventive subject matter are suitable for diagnostic and/or therapeutic (including prophylactic) purposes.

Consequently, a pharmaceutical composition may include at least one of contemplated compounds (preferably in oral or parenteral formulation) at a concentration effective to diagnose and/or treat a disease or condition associated with development and/or presence of senile plaques and/or neurofibrillary tangles, or receptor distribution or malfunction. Thus, compounds in such compositions may or may not be labeled. Most typically, compounds in diagnostic compositions will preferably be labeled with a PET detectable label (e.g., $^{11}C$ or $^{18}F$) at a specific activity that allows in vivo acquisition of a signal. Consequently, pharmaceutical or diagnostic compositions comprising compounds presented herein are especially contemplated, typically comprising a pharmaceutically acceptable carrier. Similarly, methods of imaging or treating (including prophylactic treatment) a neural disorder in a subject are contemplated in which compositions comprising compounds presented herein are administered at a dosage effective to image or treat the disorder. For example, contemplated methods of diagnosing a mammal having a disease or condition that is associated with senile plaques and neurofibrillary tangles include a step in which contemplated compounds are administered to the mammal (typically in a labeled form) at a dosage effective to locate and/or quantify in vivo binding of the labeled compound to the senile plaques and/or neurofibrillary tangles. In another example, contemplated methods of diagnosing a mammal having a disease or condition that is associated with a dysfunction, lack, or over-expression of a receptor or transporter include a step in which contemplated compounds are administered to the mammal (typically in a labeled form) at a dosage effective to locate and/or quantify in vivo binding of the labeled compound to receptor and/or transporter.

Preferably, the label is an isotope suitable for detecting the compound in vivo using PET (most preferably $^{18}F$), and contemplated compounds are typically parenterally administered. Viewed from a different perspective, compositions comprising contemplated compounds will be useful in the treatment, prevention, diagnosis and/or therapeutic follow-up of Alzheimer's disease, minimal cognitive impairment, dementia, inflammation associated with these neurological processes, inflammation as a result of other injuries, or pathophysiologies related to cancer, or will be useful in the treatment, prevention, diagnosis and/or therapeutic follow-up of certain neural (e.g., ADHD) or metabolic disorders (e.g., obesity) associated with a dysfunction, lack, or over-expression of a receptor and/or transporter.

Particularly preferred compositions according to the inventive subject matter may be administered using various routes, including orally, parenterally, by inhalation, topically, rectally, nasally, or via an implanted reservoir; wherein the term "parenteral" as used herein includes subcutaneous, intravenous, intramuscular, intrathecal, intralesional, and intracranial administration (typically injection or infusion). Preferably, the compositions are administered orally, intraperitoneally, or intravenously. Such compositions are prepared according to techniques well-known in the art of pharmaceutical formulation and may be prepared as solutions in saline, employing benzyl alcohol or other suitable preservatives, absorption promoters to enhance bioavailability and/or transport across the blood-brain barrier, fluorocarbons, and/or other conventional solubilizing or dispersing agents.

With respect to the amount of contemplated compounds in the composition, it should be recognized that the particular quantity will typically depend on the specific formulation, particular compound, and desired purpose. Therefore, it should be recognized that the amount of contemplated compounds will vary significantly. However, it is generally preferred that the compounds are present in a minimum amount effective to deliver a therapeutic effect and/or to be visualized in vitro and/or in vivo.

Thus, in most preferred embodiments, contemplated compounds will be present in a liquid carrier (single solvent or complex solvent system, preferably monophasic) in amount of between about 0.1 µg/ml to about 500 mg/ml, more typically in an amount of between about 10 µg/ml to about 100 mg/ml, and most typically between about 1 µg/ml to about 10 mg/ml. Where the formulation is a solid, contemplated compounds will be present in an amount of between about 0.1 µg/g to about 900 mg/g, more typically in an amount of between about 10 µg/g to about 500 mg/g, and most typically between about 1 mg/g to about 200 µg/g. With respect to a dosage unit, it is generally contemplated that contemplated compounds are administered at a dosage effective to achieve a desired therapeutic effect or at a dosage effective to provide visualization in vitro and/or in vivo. Therefore, suitable amounts of contemplated compounds will be in the range of 0.1 µg per dosage unit to about 0.5 gram per dosage unit, more typically between 10 µg per dosage unit to about 0.05 gram per dosage unit, and most typically between 50 µg per dosage unit to about 100 mg per dosage unit. Thus, suitable dosages will be in the range of about 0.1 µg/kg and 10 mg/kg, more typically between 1 µg/kg and 5 mg/kg, and most typically between 10 µg/kg and 1 mg/kg.

With respect to suitable labeling amounts, it is generally contemplated that all quantities are deemed suitable that can be detected using an in vitro and/or in vivo imaging technology, and particularly in vivo PET. Typically, a radiolabeling precursor compound will be labeled with a fluorine-18 source by an imaging center. For example, several microcuries to several millicuries will be produced and then used for imaging studies. Therefore, contemplated compounds and kits may also include at least one of a precursor molecule, the labeling molecule containing $^{18}F$, and the $^{18}F$ labeled ligand.

Contemplated Uses

It is generally contemplated that the compounds and compositions presented herein will be particularly useful in imaging and/or diagnostic use of conditions associated with presence of β-amyloid or other AD plaque components and/or distribution and/or dysfunction of a receptor and/or transporter. Such imaging and/or diagnostic use is preferably performed in vivo, but in vitro use is also expressly contemplated. Moreover, due to specific binding and/or uptake of contemplated compounds, therapeutic and/or prophylactic use are also deemed suitable uses. For example, suitable uses especially include treatment of various attention deficit disorders, and/or treatment of depression, schizophrenia, and numerous other mood disorders.

EXPERIMENTS

General Methods

All chemicals and solvents were of analytical or HPLC grade from Aldrich Chemical Co. and Fisher Scientific, 2-(4'-Aminophenyl)-6-hydroxybenzothiazole (also referred as 6-OH-BTA-0) was purchased from ABX Chemicals, Radeberg, Germany. Electrospray mass spectra were obtained on a Model 7250 mass spectrometer (Micromass LCT). Proton NMR spectra were recorded on a Bruker OMEGA 500 MHz spectrometer. Analytical thin layer chromatography (TLC) was carried out on silica coated plates (Baker-Flex, Phillipsburg, N.J.). Chromatographic separations were carried out on preparative TLC (silica gel GF 20×20 cm 2000 micron thick; Alltech Assoc. Inc., Deerfield, Ill.) or silica gel flash columns or semi-preparative reverse-phase columns using the Gilson high performance liquid chromatography (HPLC) systems. $^{18}F$-FDG was obtained from PETNET in sterile saline solution. Fluorine-18 radioactivity was counted in a Capintec dose calibrator while low level counting was carried out in a well-counter (Cobra quantum, Packard Instruments Co., Boston, Mass.). Radioactive thin layer chromatographs were obtained by scanning in a Bioscan system 200 Imaging scanner (Bioscan, Inc., Washington, D.C.). Human postmortem brain slices were obtained on a Leica 1850 cryotome. Fluorine-18 autoradiographic studies were carried out by exposing tissue samples on storage phosphor screens. The apposed phosphor screens were read and analyzed by OptiQuant acquisition and analysis program of the Cyclone Storage Phosphor System (Packard Instruments Co., Boston, Mass.).

Synthesis

FDGNAP: To synthesize FDGNAP, 7 µl ($5.50 \times 10^{-5}$ mole) of NAP and 5.0 mg ($2.75 \times 10^{-5}$ mole) FDG were dissolved in 0.2 mL acetate buffer (0.1M sodium acetate-acetic acid, pH4.2) and 5 µl aniline as a catalyst. The solution was left at room temperature for 4 hrs. Preparatory TLC was performed using 9:1 dichloromethane-methanol to provide FDGNAP in 31% yield MS: m/z 305 [M+H]$^+$. Aniline used as a catalyst also showed small amounts (approx. 20-30%) of the FDG adduct (MS: m/z 280 [M+Na]$^+$.

FDGBTA: For the synthesis of FDGBTA, 2.0 mg ($3.29 \times 10^{-5}$ mole) of BTA and 1.5 mg ($1.65 \times 10^{-5}$ mole) FDG was dissolved in 0.25 ml EtOH. The solution was heated for 1 hour at 99° C. Retention time of BTA was 11.3 mins while that of FDGBTA was 7.5 mins (reverse phase 10 µm C-18 HPLC column, 10×250 mm, 40% 0.1% triethylamine in water-60% acetonitrile, flow rate 1.5 mL/min). Preparatory TLC was performed using 9:1 dichloromethane-methanol solvent to extract FDGBTA in 58% yield MS: m/z 429 [M+Na]$^+$.

$^{18}F$-FDGNAP: To synthesize $^{18}F$-FDGNAP (15), 9 µL aniline catalyst and 5 µL NAP (13) was dissolved in 0.1 mL acetate buffer and 0.1 ml: of 1 mCi $^{18}F$-FDG (8, in 0.9% sterile saline) was added to this mixture. The reaction was monitored by radioTLC at 0.17, 1, 2, 3, 4 hours using the Optiquant software and product was confirmed by coelution of reference standard.

$^{18}F$-FDGBTA: For the synthesis of $^{18}F$-FDGBTA (18), 1 mg ($4.13 \times 10^{-6}$ mole) BTA (16) was dissolved in 0.2 mL EtOH and 0.1 mL of 2 to 5 mCi $^{18}F$-FDG (8, in 0.9% sterile saline) was dissolved in the solution. The solution was heated for 2 hours at 99° C. Preparatory TLC (9:1 dichloromethane-methanol) was used to isolate and purify $^{18}$F-FDGBTA (rf=0.3 for $^{18}$F-FDGBTA). The purified $^{18}$F-FDG-BTA (18) was obtained in 57% radiochemical yield with specific activities of approx. 1000 Ci/mmol. This material was used for biological studies.

In Vitro Studies $^3$H-PIB Binding: Human hippocampus sections (7 μm thick) were preincubated in 10% alcohol PBS buffer for 10 minutes. The brain sections were placed in a glass chamber and incubated with [$^3$H]-PIB (2 μCi/cc) in 10% alcohol PBS buffer, pH 7.4 at 37° C. for 1 hr. The slices were then washed with cold 10% alcohol PBS buffer (2×3 mins), cold deionized water 1 min, respectively. The brain sections were air dried, exposed overnight on a phosphor film, and then placed on the Phosphor Autoradiographic imaging System/Cyclone Storage Phosphor System (Packard Instruments Co). Regions of interest (ROIs) were drawn on the slices and the extent of binding of $^3$H-PIB was measured with DLU/mm2 using the OptiQuant acquisition and analysis program (Packard Instruments Co).

$^{11}$C-PIB Binding: Human hippocampus sections (7 μm thick) were preincubated (40% EtOH-60% deionized water) for 10 minutes. The brain sections were placed in a glass chamber and incubated with [11C]-PIB (20 μCi/cc) in 40% EtOH-60% deionized water at 37° C. for 1 hr. The slices were then washed with cold millipore water, 70%-90%-70% EtOH, water for 2,1,1,1,1 min, respectively. The brain sections were air dried, exposed overnight on a phosphor film, and then placed on the Phosphor Autoradiographic Imaging System/Cyclone Storage Phosphor System (Packard Instruments Co). Regions of interest (ROIs) were drawn on the slices and the extent of binding of 11C-PIB was measured with DLU/mm$^2$ using the OptiQuant acquisition and analysis program (Packard Instruments Co).

$^{18}$F-FDGBTA Binding: Human hippocampus sections (7 μm thick) were preincubated in 10% alcohol PBS buffer for 10 minutes. The brain sections were placed in a glass chamber and incubated with $^{18}$F-FDGBTA (2 μCi/cc) in 10% alcohol PBS buffer, pH 7.4 at 37° C. for 1 hr. The slices were then washed with cold 1.0% alcohol PBS buffer (2×3 mins), cold deionized water 1 min, respectively. The brain sections were air dried, exposed overnight on a phosphor film, and then placed on the Phosphor Autoradiographic Imaging System/Cyclone Storage Phosphor System (Packard Instruments Co). Regions of interest (ROIs) were drawn on the slices and the extent of binding of $^{18}$F-FDGBTA was measured with DLU/mm$^2$ using the OptiQuant acquisition and analysis program (Packard Instruments Co).

Results

Fluoro-2-Deoxyglucose (FDG) reacted with both the primary aliphatic amine (NAP) and the substituted aniline derivative (BTA) to provide stable products. A classical Amadori product, similar to that obtainable with glucose is not expected due to the fluorine at the C-2 atom in FDG. Reactions were carried out under aqueous as well as non-aqueous conditions with little effect on yields. Addition of aniline as a catalyst increased the yields as reported previously.

Figure 3:
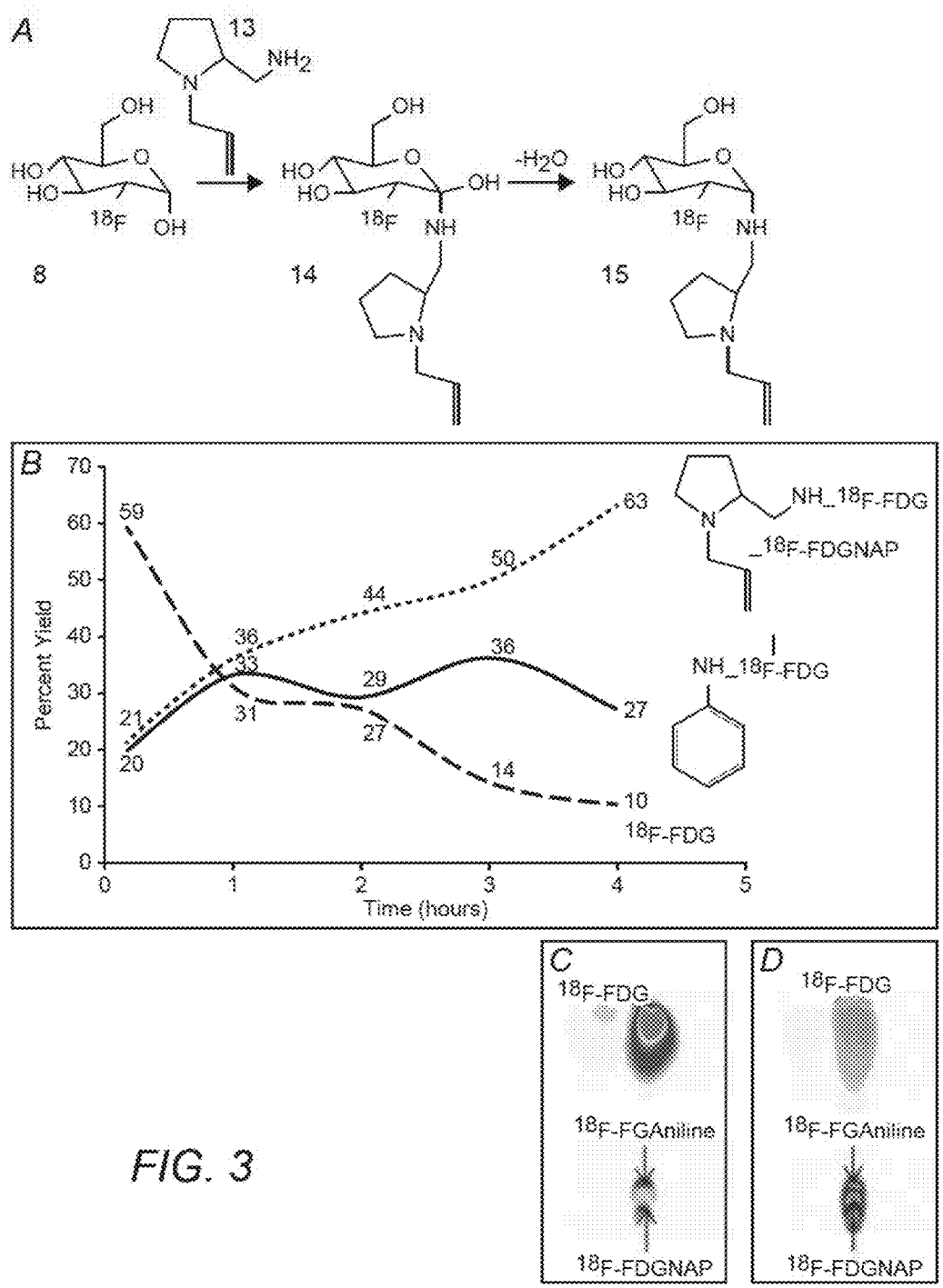
FIG. 3 depicts an exemplary reaction sequence for production of $^{18}$F-FDGNAP and associated time course and TLC traces.
Figure 4:
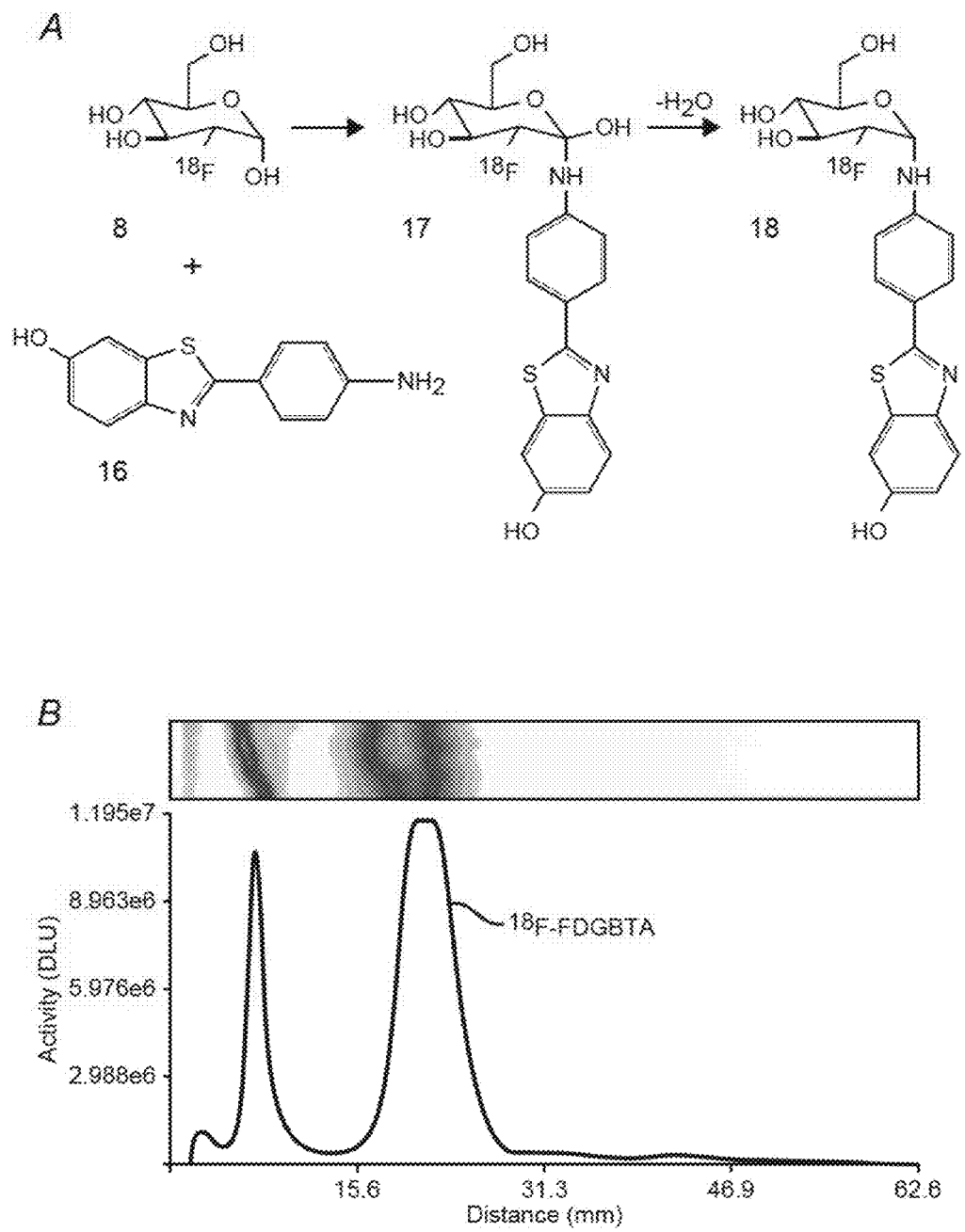
FIG. 4 depicts an exemplary reaction sequence for production of $^{18}$F-FDGBTA and an associated TLC trace.

Based on the findings with unlabeled FDG, an $^{18}$F-FDGly quasi-Amadori product was expected front the reaction of $^{18}$F-FDG with NAP as shown in FIG. 3, Panel A, and BTA as shown in FIG. 4, Panel A. The reaction kinetics of $^{18}$F-FDG with NAP at room temperature was monitored by radioTLC at 0.17, 1, 2, 3, 4 hrs as is shown in FIG. 3, Panels C and D. Panel C shows the radioTLC of $^{18}$F-FDGNAP reaction mixture at 10 mins of reaction time, showing presence of product along with some $^{18}$F-FDG, and Panel D shows the radioTLC at 4 hrs of reaction time showing significant increase in product. Thus, over time the $^{18}$F-FDGNAP product increased and the $^{18}$F-FDG decreased as is plotted in FIG. 3, Panel B. The amount of $^{18}$F-FDGaniline was consistently around 25-30% in solution and served as an intermediate product for the formation of $^{18}$F-FDGNAP. $^{18}$F-FDGNAP increased over time from 21 to 63% while $^{18}$F-FDG decreased to 10% in 4 hrs.

Similarly in FIG. 4, the reaction of BTA with $^{18}$F-FDG is depicted in Panel A and was carried out in ethanol without the catalyst, aniline and thus required heating. The radioactive product $^{18}$F-FDG BTA was purified by radioTLC in 57% yield and few significant side products were observed as is evident in Panel B of FIG. 4.

Thus, it should be appreciated that the (radio)synthesis of fluorodeoxyglycosylamines can be performed at moderate temperatures (e.g., 20-50° C.) by the addition of the substituted amines to FDG and may be akin to click chemistry. Therefore, this method may be applied generally to various amines using the simple reaction conditions described here, similar to click chemistry approaches with other substrates having a primary amine group.

Figure 5:
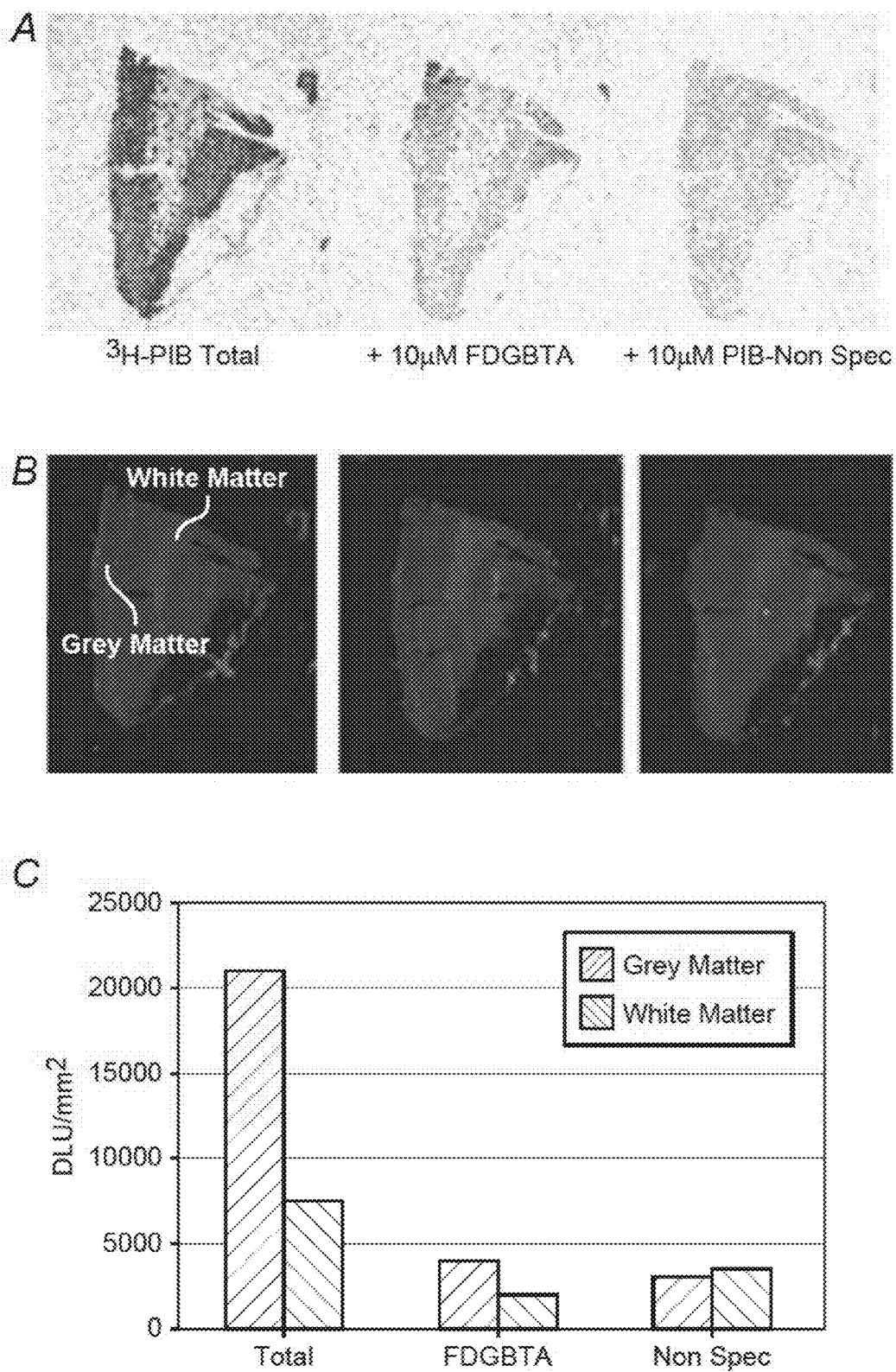
FIG. 5 depicts results from tissue labeling using $^3$H-PIB, where Panel A shows a human postmortem brain autoradiograph with total $^3$H-PIB binding to AD brain slices (left), competition with 10 μM FDGBTA (middle), and nonspecific binding, 10 μM PIB (right). Panel B depicts the corresponding photomicrographs for Panel A, and Panel C is a graphic result of binding.

Since FDGBTA is an analog of PIB, which is known to bind to human Aβ-amyloid plaques, the inventors tested competition of both PIB and FDGBTA with postmortem human brain Aβ-amyloid sites labeled with $^3$H-PIB as is illustrated in Panel A of FIG. 5, with the corresponding photomicrographs in Panel B of FIG. 5. Preliminary studies indicated that at 10 μM concentration, $^3$H-PIB was displaced from the Aβ-plaque binding sites by FDGBTA and PIB and the reduction in the grey matter areas was >80% (see graph in Panel C of FIG. 5, showing the relative displacement of $^3$H-PIB by FDGBTA based on autoradiographs in the grey and white matter).

Figure 6:
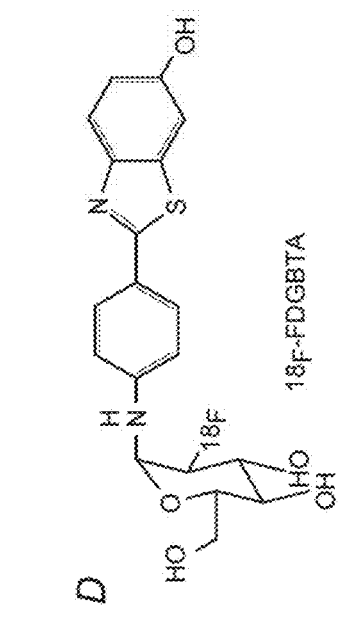
FIG. 6 depicts selected radio labeled compounds (Panels A and D) and corresponding results from tissue labeling using the radio labeled compounds (Panels B and E). Panels C and F are graphic results of binding.
Figure 6:
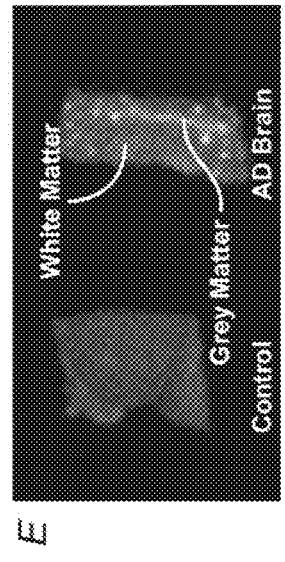
Figure 6:
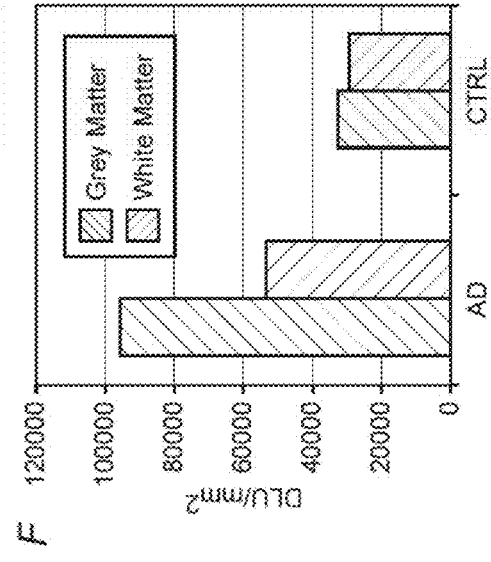
Figure 6:
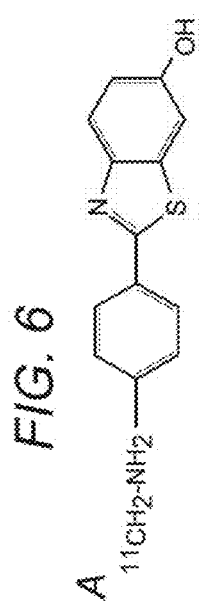
Figure 6:
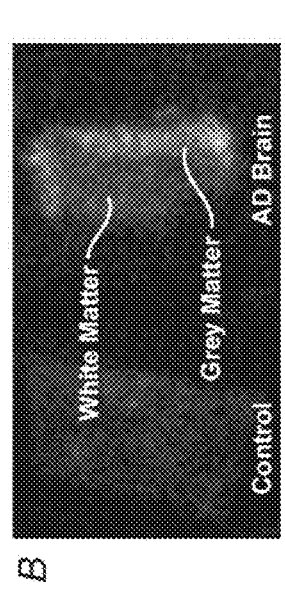
Figure 6:
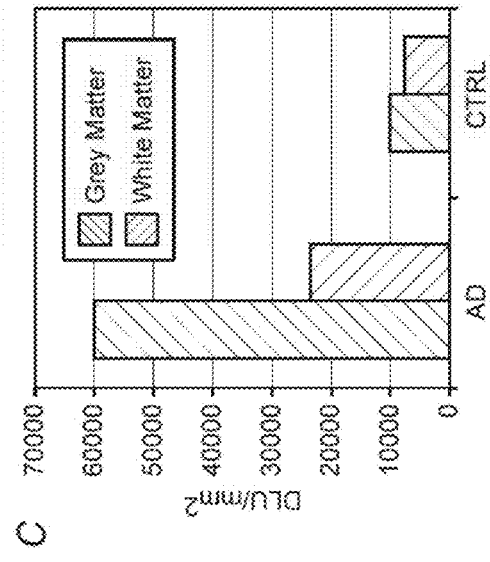

Radiolabeled $^{18}$F-FDGBTA (Panel D, FIG. 6) was evaluated and compared with $^{11}$C-PIB (Panel A, FIG. 6) for binding to postmortem human brain Aβ-amyloid sites. As expected $^{11}$C-PIB exhibited significant binding to AD brain grey matter as reported previously (Panel B, FIG. 6) whereas binding of $^{18}$F-FDGBTA was found to be non-uniform, but exhibited regions of high binding (Panel E, FIG. 6) [14]. The ratio of AD brain versus control subjects was 6 for $^{11}$C-PIB, while that for $^{18}$F-FDGBTA was 3. In contrast, $^{18}$F-FDG did not exhibit any binding to grey matter areas of AD subjects. These findings suggest that $^{18}$F-FDGBTA is stable in vitro and exhibits biological properties similar to $^{11}$C-PIB with lower ratios, suggesting that either the affinity of FDGBTA may be lower than PIB or there may be additional sites of binding due to a significant difference in the size of the substituent ($^{11}$C-methyl in PIB versus $^{18}$F-FDG in FDG-BTA). Panels C and F depict graphs showing the relative binding of $^{11}$C-PIB and $^{18}$F-FDGBTA, respectively, on control versus AD brain slices based in autoradiographs. Therefore, it should be appreciated that these results indicate that $^{18}$F-fluordeoxyglycosylamines are stable in vitro and exhibit desirable biological properties.

To further increase in vivo stability, reductive amination of $^{18}$F-FDGly was performed to provide reduced FDGly ($^{18}$F-rFGDly, see structure below). These $^{18}$F-rFDGly compounds may be particularly useful as PET imaging agents in vivo since they have the potential of linking $^{18}$F-FDG (hydrophilic) to various lipophilic molecules containing an amine group.

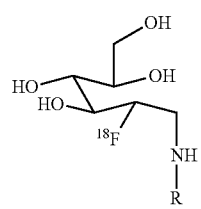

One exemplary general method of synthesis for a reduced rFGDly is shown in FIG. 7. Here, FDG or $^{18}$F-FDG and a substituted amine (NH$_2$—R) are dissolved in an alcohol or other suitable solvent (e.g., methanol or ethanol) with trace amounts of acetic acid and allowed to react at room temperature or at elevated temperature (e.g., up to 110° C.) for 30 mins to one hour in the presence or absence of molecular sieves. The reaction mixture is then cooled in a ice water bath and sodium cyanoborohydride or other reducing agent is added and allowed to react for 30 mins to one hour. The final product is isolated by chromatography. In the same manner, various other compounds may also be prepared as exemplarily shown in the following:

rFDGNAP: FDG was used for reductive amination with (N-allyl-2-aminomethylpyrrolidine (NAP) to synthesize rFDGNAP

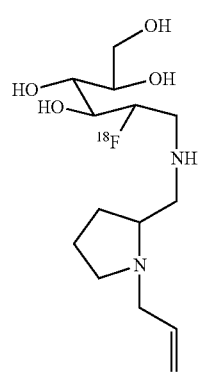 [SMILES: C=CCN1CCCC1CNCC([18F])C(O)C(O)C(O)CO]

rFDGDASA: FDG was used for reductive amination with 4-Amino-4'-(N,N-dimethyl-amino)stilbene (DASA) to synthesize rFDGDASA, which may be particularly suitable for radiolabeling norepinephrine terminals

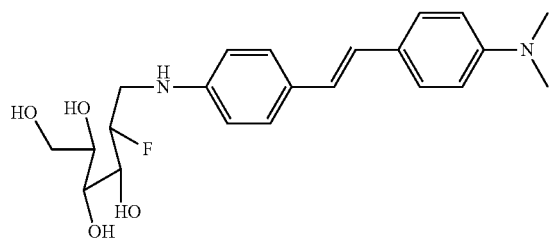 [SMILES: CN(C)c1ccc(/C=C/c2ccc(NCC(F)C(O)C(O)C(O)CO)cc2)cc1]

rFDGBTA: Reductive amination was carried out at room temperature using an anhydrous solution of molecular sieves, methanol and acetic acid. The yield for the reduced rFDGBTA was 94%. Human brain homogenate assay of rFDGBTA for Aβ-Amyloid plaques was investigated. The homogenate was suspended in different concentrations of rFDGBTA ($10^{-11}$ to $10^{-4}$M) in the assay buffer (PBS buffer, 10% alcohol, pH 7.4). Nonspecific binding was determined by including $^3$H-PIB. Total assay volume was 0.25 ml. Displacement binding study with $^3$H-PIB binding curve suggests that rFDGBTA may have 100 times weaker binding compared to PIB.

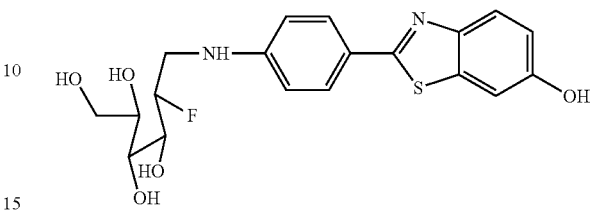

[18]F-rFDGTAZA: FDG was combined with N,N-Dimethyl-4-4'-azodianliline (DAZA) to synthesize rFDGDAZA. For radiosynthesis, $^{18}$F-FDG was reacted with DAZA to synthesize [18]F-rFDGDAZA. The synthesis was successful with 36% yield. [18]F-rFDGDAZA is expected to bind to Alzheimer's disease (AD) hippocampus and AD plaque.

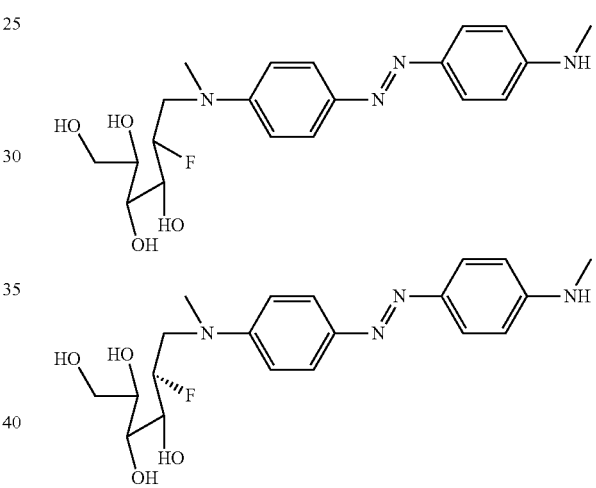

Figure 8:
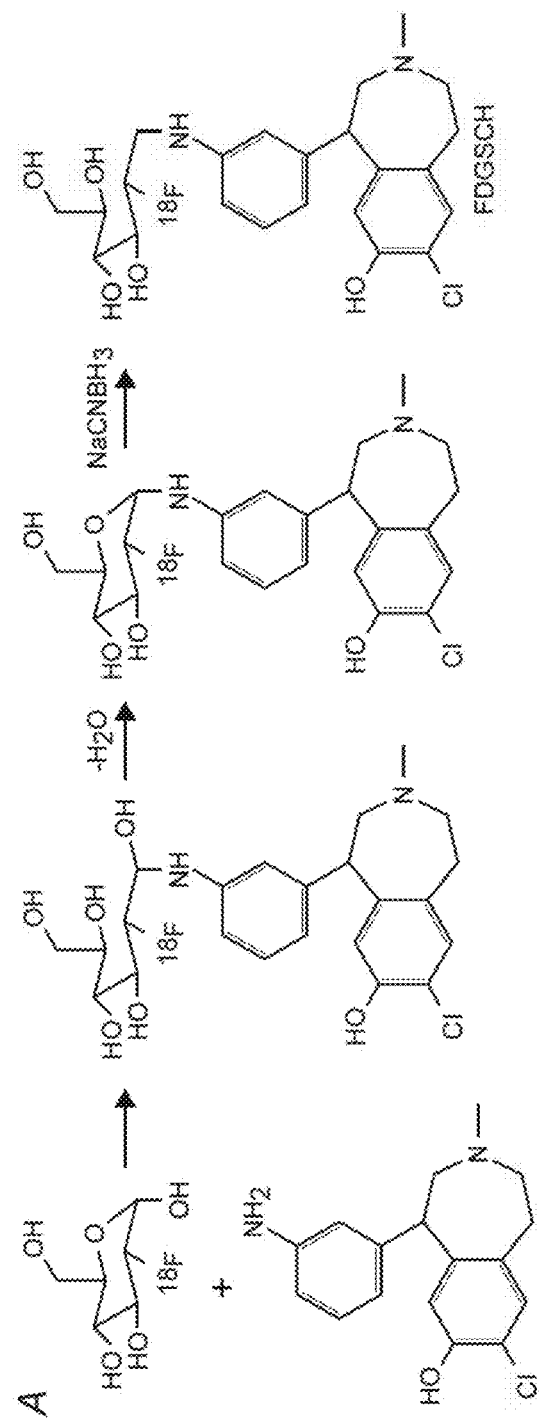
FIG. 8 depicts an exemplary reaction sequence for production of $^{18}$F-FDGSCH and associated labeling and binding plot.
Figure 8:
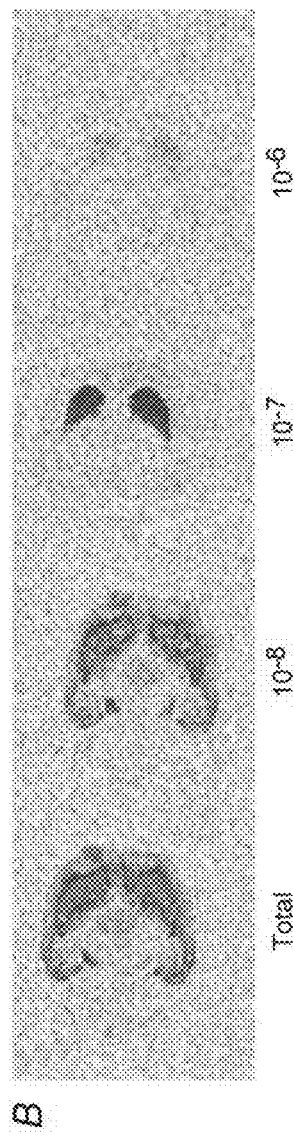

[18]F-rFDGSCH: FIG. 8 exemplarily shows in Panel A synthesis of $^{18}$F-FDGSCH following the same protocol as outlines above. Here, $^{18}$F-FDG was successfully coupled to SCH38548, which is a dopamine D-1 receptor antagonist. Subsequent in vitro studies indicated that the binding properties of $^{18}$F-FDGSCH for the D-1 receptor in D-1 receptor rich regions in rat brains were retained at nanomolar affinities. More specifically, Panel (B) of FIG. 8 shows displacement of $^3$H-SCH 23390 in the striatum (red) by increasing concentration of FDGSCH in rat brain slices, and Panel C of FIG. 8 shows a binding affinity curve of FDGSCH for D-1 receptors in rat brains.

In yet another example, [18]F-rFDGMK801 was prepared in a manner as outlined above. In this case, the affinity ligand is a ligand for the N-methyl-D-aspartate (NMDA) receptor, which is a major receptor subtype of the excitatory amino acid (EAA) neurotransmitters, glutamate and aspartate in the mammalian central nervous system (CNS). As the NMDA receptors belong to the family of excitatory ionotropic glutamate receptors and are the likely cause of neuronal death under excitotoxic pathological conditions, compounds for labeling are thought of be of value for diagnostic and even therapeutic purposes.

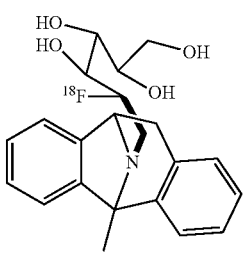

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . , and N, the text should be interpreted as requiring only one element from the group, not A plus N, or B plus N, etc. Moreover, as used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

What is claimed is:

1. A compound having the structure of Formula VIII

Formula VIII

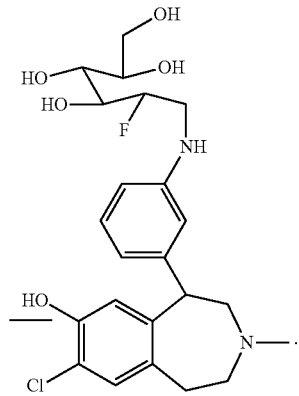

2. The compound of claim 1, wherein F is $^{18}$F.

3. A pharmaceutical composition comprising the compound of claim 1 in combination with a pharmaceutically acceptable carrier.

4. The pharmaceutical composition of claim 3 wherein F is $^{18}$F and wherein the compound is present in an amount effective to produce an in vivo detectable PET signal.

* * * * *